United States Patent [19]

Noguchi et al.

[11] 4,447,260
[45] May 8, 1984

[54] N-SUBSTITUTED PHENYL-1-METHYLCYCLOPROPANECARBOXAMIDES, AND THEIR HERBICIDAL USE

[75] Inventors: Hiroshi Noguchi, Toyonaka; Ryo Yoshida, Kawanishi; Seizo Sumida, Nishinomiya; Katsuzo Kamoshita, Osaka, all of Japan

[73] Assignee: Sumitomo Chemical Company, Limited, Osaka, Japan

[21] Appl. No.: 319,100

[22] Filed: Nov. 6, 1981

[30] Foreign Application Priority Data

Nov. 10, 1980 [JP] Japan .................. 55-158526

[51] Int. Cl.³ .................. A01N 53/00; C07C 103/737
[52] U.S. Cl. ...................................... 71/118; 564/190
[58] Field of Search .......................... 564/190; 71/118

[56] References Cited

U.S. PATENT DOCUMENTS 3,277,171 10/1966 Hopkins .................. 564/190
4,166,735 9/1979 Pilgram et al. .................. 564/190
4,199,347 8/1980 Pilgram et al. .................. 71/118

FOREIGN PATENT DOCUMENTS 1593932 7/1981 United Kingdom .

Primary Examiner—Natalie Trousof
Assistant Examiner—L. Hendriksen
Attorney, Agent, or Firm—Birch, Stewart, Kolasch & Birch

[57] ABSTRACT

A compound of the formula:

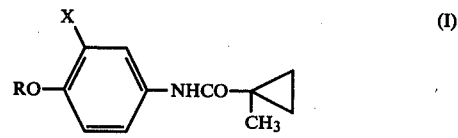

wherein R is a lower alkyl group substituted with two or three fluorine atoms and X is a halogen atom, a lower alkyl group or a trifluoromethyl group, which is useful as a herbicide against a variety of weeds with a high selectivity to cotton, wheat and rice plants.

8 Claims, No Drawings

N-SUBSTITUTED PHENYL-1-METHYLCYCLOPROPANECARBOX-AMIDES, AND THEIR HERBICIDAL USE

The present invention relates to N-substituted phenyl-1-methylcyclopropanecarboxamides, and their production and use.

The said N-substituted phenyl-1-methylcyclopropanecarboxamides (hereinafter referred to as "carboxamide(s)") are representable by the formula:

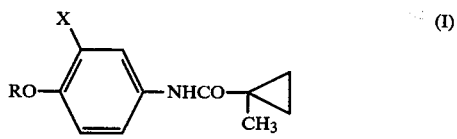

wherein R is a lower alkyl group (e.g. methyl, ethyl) substituted with two or three fluorine atoms and X is a halogen atom (e.g. chlorine, bromine, iodine, fluorine), a lower alkyl group (e.g. methyl, ethyl) or a trifluoromethyl group and are useful as herbicides.

Rice plants, wheat, cotton and the like are crop plants of world-wide importance and, in the cultivation of these crop plants, the chemical control of weeds is necessary to prevent reductions in the yield. Particularly, it is a recent demand that herbicides to be applied to these crop plants have a selectivity, i.e. a high potency against weeds with no or substantially no damage to the crop plants. On the other hand, it is frequently observed that herbicides showing a selectivity to certain kinds of crop plants can hardly exterminate weeds belonging to the same classification as the crop plants. For instance, diuron (3-(3,4-dichlorophenyl)-1,1-dimethylurea) and fluometuron (1,1-dimethyl-3-(3-trifluoromethylphenyl)urea) are major herbicides applicable to the field of cotton but can not exert a sufficient herbicidal effect on prickly sida (*Sida spinosa* L.), which causes a serious problem in such fields. This is probably due to the fact that both cotton and prickly sida belong to Malvaceae. Therefore, favorable herbicides to be applied to the field of cotton are required to exert a high herbicidal effect on prickly sida without causing any chemical injury to cotton. In addition, it is generally very difficult to discover any herbicidal compound having a high selectivity which can be used by foliar treatment.

As a result of an extensive study, it has now been found that the carboxamides (I) show a broad herbicidal spectrum against a variety of weeds including prickly sida with a high selectivity to cotton. It has also been found that the carboxamides (I) exhibit a notable selectivity to wheat by foliar treatment. It has further been found that under flooded conditions, the carboxamides (I) show a strong herbicidal effect on weeds without causing any chemical injury to the rice plant.

Examples of weeds against which the carboxamides (I) can exert a herbicidal activity are dicotyledoneous weeds such as prickly sida (*Sida spinosa*), cocklebur (*Xanthium pennsylvanicum*), tall morningglory (*Ipomoea purpurea*), sicklepod (*Cassia obtusifolia*), jimsonweed (*Datura stramonium*), black nightshade (*Solanum nigrum*), velvetleaf (*Abutilon theophrasti*), redroot pigweed (*Amaranthus retroflexus*), smartweed sp. (Polygonum spp.), common lambsquarters (*Chenopodium album*), common chickweed (*Stellaria media*), wild buckwheat (*Polygonum convolvulus*), pansy (*Viola tricolor*), common groundsel (*Senecio vulgaris*), bedstraw (*Galium aparine*), henbit (*Lamium amplexicaule*), pineappleweed (*Matricaria matricarioides*), toothcup (*Rotala* spp.), false pimpernel (*Lindernia pyxidaria*), wild mustard (*Sinapis arvensis*), oxeye daisy (*Chrysanthemum segetum*), red poppy (*Papaver rhoeas*) and field pansy (*Viola arvensis*), monocotyledoneous weeds such as barnyardgrass (*Echinocloa crus-galli*), green foxtail (*Setaria viridis*), wild oat (*Avena fatua*), blackgrass (*Alopecurus myosuroides*), annual bluegrass (*Poa annua*), Italian ryegrass (*Lolium multiflorum*), downy brome (*Bromus tectorum*), quackgrass (*Agropyron repens*) and pickerel weed (*Monochoria vaginalis*), Cyperus grasses such as nutsedge sp. (*Cyperus difformis*) and nutsedge (*Cyperus Iria* L.), etc.

While the carboxamides (I) are novel, there are known some compounds similar to them in chemical structure. For instance, U.S. Pat. No. 4,166,735 discloses N-(3-chloro-4-isopropoxyphenyl)-1-methylcyclopropanecarboxamide (Control (a)). However, the said U.S. patent is entirely silent on the selectivity of this compound to cotton. In fact, it was experimentally confirmed that Control (a) is inferior to the carboxamides (I) in herbicidal effect and produces chemical injury to cotton. Further, for instance, U.S. Pat. No. 3,277,171 discloses N-(3,4-dichlorophenyl)-1-methylcyclopropanecarboxamide (Control (b)). However, this compound is inferior to the carboxamides (I) not only in selectivity to cotton but also in herbicidal potency against weeds such as prickly sida, cocklebur and sicklepod.

As stated above, the carboxamides (I) have a high selectivity to cotton, wheat and rice plants and therefore are useful as herbicides for the fields of those plants. It is particularly notable that their herbicidal potency on prickly sida is much superior to that of commercially available herbicides for cotton such as diuron and fluometuron. It is also notable that they exhibit a high herbicidal potency against common chickweed (*Stellaria media* L.) and pansy (*Viola tricolor*), which can hardly be exterminated with bromoxynil (3,5-dibromo-4-hydroxybenzonitrile) known as a herbicide for foliar treatment in the field of wheat. It is further notable that under the flooded condition, they are more effective in extermination of Gramineae grasses than MCP (4-chloro-2-methylphenoxyacetic acid) known as a herbicide applicable to the paddy fields of rice plants. Besides, due to their high herbicidal potency and broad herbicidal spectrum, they may be used as herbicides for orchards, fruit gardens, forests, non-agricultural fields, etc.

The carboxamides (I) can be prepared by reacting an aniline compound of the formula:

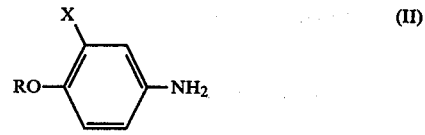

wherein R and X are each as defined above with 1-methylcyclopropanecarboxylic acid or its reactive derivative (e.g. acid anhydride, acid halide, acid ester), usually in a molar ratio of about 1:1 to 2:1, in the presence or absence of an inert solvent (e.g. acetone, acetonitrile, benzene, toluene, xylene, diethyl ether, tetrahydrofuran, dioxane, dichloromethane, chloroform, carbon tetrachloride, ethyl acetate, pyridine, dimethylformamide, dimethylsulfoxide, water) at a temperature from about −10° to 100° C. When the 1-methylcyclopropanecarboxylic acid is used in the free form, the presence of a dehydrating agent such as a carbodiimide (e.g. N,N'-dicyclohexylcarbodiimide) or a condensing agent such as phosphorus oxychloride, thionyl chloride or phosgene in the reaction system is preferred. When the 1-methylcyclopropanecarboxylic acid is used in the form of an acid halide, the presence of a dehydrohalogenating agent such as an inorganic basic substance (e.g. sodium hydrogen carbonate, potassium hydrogen carbonate, sodium carbonate, potassium carbonate, sodium hydroxide, potassium hydroxide) or an organic basic substance (e.g. triethylamine, tributylamine, pyridine, pyrimidine) in the reaction system is favorable. The reaction time is largely dependent upon the reaction temperature and the kind of the reagent, but it may be usually within about 10 hours. Recovery of the objective carboxamide (I) from the reaction mixture may be effected by a per se conventional separation procedure such as solvent extraction, column chromatography, distillation and/or recrystallization.

Among the starting aniline compounds, some of them are known. For instance, 3-chloro-4-difluoromethoxyaniline, 3-trifluoromethyl-4-difluoromethoxyaniline, 3-chloro-4-trifluoromethoxyaniline, etc. are described in German Offenlegungsschrift Nos. 2113978, 2801316, 2601780, etc. Others are novel. These known and novel aniline compounds (II) may be produced by various procedures, for instance, as disclosed in J. Org. Chem., 25, page 2009 (1960) or Japanese Patent Publication (unexamined) No. 36467/1981. One of the typical procedures is representable by the formulas:

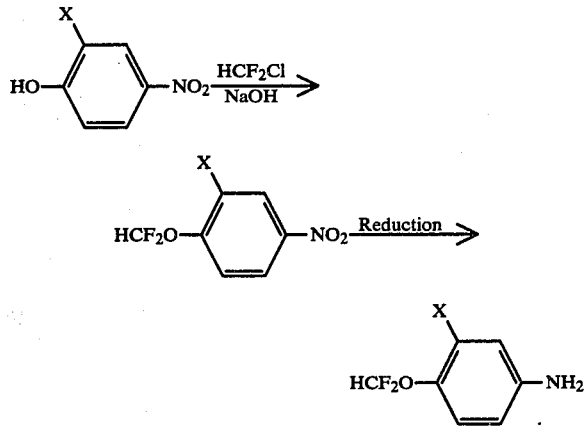

wherein X is as defined above.

Some of the preferred embodiments of the procedure for preparing the carboxamides (I) are shown below.

EXAMPLE 1

Production of 3-bromo-4-difluoromethoxyaniline:

2-Bromo-4-nitrophenol (10.9 g) was dissolved in dioxane (60 ml), a solution of sodium hydroxide (18.4 g) in water (50 ml) was added thereto, and the resulting mixture was heated up to 60° C. while stirring vigorously. Chlorodifluoromethane gas was introduced therein, whereby the generation of heat was initiated. The reaction was continued for about 40 minutes. The reaction mixture was cooled to room temperature, poured onto ice-water and extracted with ether. The extract was washed with water and saturated sodium chloride solution, dried over anhydrous magnesium sulfate and concentrated under reduced pressure to give 3-bromo-4-difluoromethoxynitrobenzene (8.7 g) as a pale yellow oil. $n_D^{20.5}$ 1.5500.

NMR $\delta^{CDCl_3}$ (ppm): 6.68 (1H, t, J=72 Hz), 7.33 (1H, d, J=9 Hz), 8.21 (1H, d.d., J=9 Hz, 3 Hz), 8.45 (1H, d, J=3 Hz).

The above obtained 3-bromo-4-difluoromethoxynitrobenzene was reduced catalytically using platinum dioxide as a catalyst in ethanol to give 3-bromo-4-difluoromethoxyaniline. $n_D^{22.5}$ 1.5240.

NMR $\delta^{CDCl_3}$ (ppm): 4.00 (2H, br. s), 6.30 (1H, t, J=74 Hz), 6.46 (1H, d.d., J=7 Hz, 3 Hz), 6.78 (1H, d, J=3 Hz), 6.88 (1H, d, J=7 Hz).

In the same manner as above, the following nitrobenzene and aniline compounds (II) were produced:
3-Fluoro-4-difluoromethoxynitrobenzene, $n_D^{20.5}$ 1.4961;
3-Methyl-4-difluoromethoxynitrobenzene, $n_D^{25.5}$ 1.5192;
3-Fluoro-4-difluoromethoxyaniline, $n_D^{20.5}$ 1.4910;
3-Methyl-4-difluoromethoxyaniline, $n_D^{25}$ 1.5087.

EXAMPLE 2

Production of 3-chloro-4-(2,2,2-trifluoroethoxy)aniline:

Oily sodium hydride (50%, 5.7 g) was washed with hexane and added to dimethylformamide (100 ml). 2,2,2-Trifluoroethanol (5.7 g) was dropwise added thereto while stirring and ice-cooling. After the dropwise addition was completed, stirring was continued for 10 minutes, and then a solution of 3-chloro-4-fluoronitrobenzene (17.6 g) in dimethylformamide (50 ml) was dropwise added thereto. Stirring was carried out at about 120° C. for 2 hours. The reaction mixture was poured onto ice-water and extracted with ether. The extract was washed with saturated sodium chloride solution, dried over anhydrous magnesium sulfate and concentrated to give 3-chloro-(2,2,2-trifluoroethoxy)nitrobenzene (22 g) as pale yellow crystals. M.P., 50°–51° C.

NMR $\delta^{CDCl_3}$ (ppm): 4.49 (2H, qualtet, J=8 Hz), 6.99 (1H, d, J=9 Hz), 8.13 (1H, d.d., J=9 Hz, 2 Hz), 8.30 (1H, d, J=2 Hz).

The above obtained 3-chloro-4-(2,2,2-trifluoroethoxy)nitrobenzene was catalytically reduced using platinum dioxide in ethanol to give 3-chloro-4-(2,2,2-trifluoroethoxy)aniline. M.P., 50°–52° C.

NMR $\delta^{CDCl_3}$ (ppm): 3.85 (2H, br. s), 4.25 (2H, qualtet, J=8 Hz), 6.45 (1H, d.d., J=9 Hz, 2 Hz), 6.66 (1H, d, J=2 Hz), 6.81 (1H, d, J=9 Hz).

EXAMPLE 3

Production of N-(3-chloro-4-difluoromethoxyphenyl)-1-methylcyclopropanecarboxamide (Compound No. 1):

To a solution of 3-chloro-4-difluoromethoxyaniline (1.95 g) in methylene chloride (50 ml), triethylamine (1.1 g) was added, and a solution of 1-methylcyclopropanecarbonyl chloride (1.2 g) in methylene chloride was dropwise added while cooling with ice-water. The reaction mixture was stirred at room temperature for 1 hour, admixed with water and extracted with ether. The extract was washed with 1 N hydrochloric acid, sodium hydrogen carbonate solution and saturated sodium chloride solution, dried over anhydrous magnesium sulfate and concentrated to give crude crystals (2.6 g). Recrystallization from ethanol gave N-(3-chloro-4- difluoromethoxyphenyl)-1-methylcyclopropanecarboxamide (2.2 g). M.P., 59°-60° C.

Anal. Calcd. for $C_{12}H_{12}ClF_2NO_2$: C, 52.27%; H, 4.39%; N, 5.08%; Cl, 12.86%. Found: C, 52.51%; H, 4.34%; N, 5.16%; Cl, 12.60%.

NMR $\delta^{CDCl_3}$ (ppm): 0.65 (2H, m), 1.20 (2H, m), 1.40 (3H, s), 6.38 (1H, t, J=74 Hz), 6.90 (1H, d, J=8 Hz), 7.20 (1H, d.d., J=8 Hz, 2 Hz), 7.59 (1H, d, J=2 Hz), 7.96 (1H, br. s).

IR $\nu^{Nujol}$ (cm$^{-1}$): 3280, 1640, 1585, 1490, 1130, 1030, 870, 815, 785.

EXAMPLE 4

Production of N-(3-bromo-4-difluoromethoxyphenyl)-1-methylcyclopropanecarboxamide (Compound No. 3):

In the same manner as in Example 3 but using 3-bromo-4-difluoromethoxyaniline (2.4 g) and 1-methylcyclopropanecarbonyl chloride (1.2 g) with pyridine (0.8 g) as the hydrogen chloride-eliminating agent and ethyl acetate as the solvent, the operations were effected to give N-(3-bromo-4-difluoromethoxyphenyl)-1-methylcyclopropanecarboxamide (3.1 g). M.P., 71°-71.5° C.

EXAMPLE 5

Production of N-(3-methyl-4-difluoromethoxyphenyl)-1-methylcyclopropanecarboxamide (Compound No. 4):

To a mixture of toluene (50 ml) and pyridine (4.2 g) cooled at 0° C., thionyl chloride (1.3 g) was added, and a solution of 1-methylcyclopropanecarboxylic acid (1.0 g) in toluene was dropwise added thereto while stirring. A solution of 3-methyl-4-difluoromethoxyaniline (1.75 g) in toluene was dropwise added thereto. After the dropwise addition was completed, stirring was continued at room temperature for 3 hours. The reaction mixture was admixed with 5% hydrochloric acid (20 ml). The organic solvent layer was separated, washed with 1% sodium hydroxide solution and saturated sodium chloride solution, dried over anhydrous sodium sulfate and concentrated to give crude crystals (2.2 g). The crude crystals were recrystallized from ethanol to give N-(3-methyl-4-difluoromethoxyphenyl)-1-methylcyclopropanecarboxamide (1.8 g). M.P., 68°-69° C.

EXAMPLE 6

Production of N-(3-trifluoromethyl-4-difluoromethoxyphenyl)-1-methylcyclopropanecarboxamide (Compound No. 5):

To a solution of 1-methylcyclopropanecarboxylic acid (1.0 g) in tetrahydrofuran (50 ml), 3-trifluoromethyl-4-difluoromethoxyaniline (2.25 g) was added, and a solution of N,N'-dicyclohexylcarbodiimide (DCC) (2.2 g) in tetrahydrofuran was dropwise added while stirring. After several minutes, the by-produced N,N'-dicyclohexylurea (DCU) was eliminated by filtration. To the filtrate, acetic acid (2 ml) was added to decompose excessive DCC, followed by elimination of DCU. The resultant filtrate was extracted with ether, and the extract was washed with 1 N hydrochloric acid, sodium hydrogen carbonate solution and saturated sodium chloride solution, dried over anhydrous magnesium sulfate and concentrated. The crude crystals (2.85 g) were recrystallized from ethanol to give N-(3-trifluoromethyl-4-difluoromethoxyphenyl)-1-methylcyclopropanecarboxamide (2.5 g). M.P., 39°-40° C.

EXAMPLE 7

Production of N-(3-chloro-4-(2,2,2-trifluoroethoxy)-phenyl)-1-methylcyclopropanecarboxamide (Compound No. 7):

To a solution of 1-methylcyclopropanecarboxylic acid (1.8 g) in pyridine (50 ml), a solution of 3-chloro-4-(2,2,2-trifluoroethoxy)aniline (2.3 g) in pyridine (10 ml) cooled with ice was dropwise added while stirring. After stirring at room temperature for 10 hours, the reaction mixture was admixed with water and extracted with ether. The extract was washed with 1 N hydrochloric acid, sodium hydrogen carbonate solution and saturated sodium chloride solution, dried over anhydrous magnesium sulfate and concentrated. The crude crystals (2.8 g) were recrystallized from ethanol to give N-(3-chloro-4-(2,2,2-trifluoroethoxy)phenyl)-1-methylcyclopropanecarboxamide (2.6 g). M.P., 95°-96° C.

EXAMPLE 8

Production of N-(3-chloro-4-trifluoromethoxyphenyl)-1-methylcyclopropanecarboxamide (Compound No. 6):

To a solution of 3-chloro-4-trifluoromethoxyaniline (2.1 g) in methylene chloride (50 ml), triethylamine (1.1 g) was added, and a solution of 1-methylcyclopropanecarbonyl chloride (1.2 g) in methylene chloride was dropwise added thereto while stirring and ice-cooling. After stirring at room temperature for 1 hour, the reaction mixture was washed with 1 N hydrochloric acid, sodium hydrogen carbonate solution and saturated sodium chloride solution, dried over anhydrous magnesium sulfate and concentrated. The crude crystals (2.9 g) were recrystallized from ethanol to give N-(3-chloro-4-trifluoromethoxyphenyl)-1-methylcyclopropanecarboxamide (2.6 g). M.P., 101°-102° C.

Anal. Calcd. for $C_{12}H_{11}ClF_3NO_2$: C, 49.08%; H, 3.78%; N, 4.77%; Cl, 12.07%. Found: C, 48.92%; H, 3.81%; N, 4.60%; Cl, 12.30%.

NMR $\delta^{CDCl_3}$ (ppm): 0.75 (2H, m), 1.30 (2H, m), 1.46 (3H, s), 7.3 (2H, m), 7.54 (1H, br. s), 7.76 (1H, d, J=2 Hz).

EXAMPLE 9

Production of N-(4-difluoromethoxy-3-fluorophenyl)-1-methylcyclopropanecarboxamide (Compound No. 2):

To a solution of 3-fluoro-4-difluoromethoxyaniline (1.8 g) in methylene chloride (50 ml), triethylamine (1.1 g) was added, and a solution of 1-methylcyclopropanecarbonyl chloride (1.2 g) in methylene chloride was dropwise added thereto while stirring and ice-cooling. After stirring at room temperature for 1 hour, the reaction mixture was admixed with water and extracted with ether. The extract was washed with 1 N hydrochloric acid, sodium hydrogen carbonate solution and saturated sodium chloride solution, dried over anhydrous magnesium sulfate and concentrated. The oily residue (2.5 g) was chromatographed on silica gel and eluted with a mixture of hexane and acetone to give N-(4-difluoromethoxy-3-fluorophenyl)-1-methylcyclopropanecarboxamide (2.2 g). $n_D^{24}$ 1.5061.

Anal. Calcd. for $C_{12}H_{12}F_3NO_2$: C, 55.60%; H, 4.67%; N, 5.40%. Found: C, 55.42%; H, 4.71%; N, 5.55%.

NMR $\delta^{CDCl_3}$ (ppm): 0.66 (2H, m), 1.22 (2H, m), 1.40 (3H, s), 6.49 (1H, t, J=74 Hz), 6.9-7.7 (3H), 7.70 (1H, br. s).

The products in Examples 3 to 9 are listed as follows:

| Compound No. | Structure | Physical property |
|---|---|---|
| 1 | HCF$_2$O—⟨C$_6$H$_3$(Cl)⟩—NHCO—⟨cyclopropyl⟩—CH$_3$ | M.P. 59–60° C. |
| 2 | HCF$_2$O—⟨C$_6$H$_3$(F)⟩—NHCO—⟨cyclopropyl⟩—CH$_3$ | $n_D^{24}$ 1.5061 |
| 3 | HCF$_2$O—⟨C$_6$H$_3$(Br)⟩—NHCO—⟨cyclopropyl⟩—CH$_3$ | M.P. 71–71.5° C. |
| 4 | HCF$_2$O—⟨C$_6$H$_3$(H$_3$C)⟩—NHCO—⟨cyclopropyl⟩—CH$_3$ | M.P. 68–69° C. |
| 5 | HCF$_2$O—⟨C$_6$H$_3$(F$_3$C)⟩—NHCO—⟨cyclopropyl⟩—CH$_3$ | M.P. 39–40° C. |
| 6 | CF$_3$O—⟨C$_6$H$_3$(Cl)⟩—NHCO—⟨cyclopropyl⟩—CH$_3$ | M.P. 101–102° C. |
| 7 | CF$_3$CH$_2$O—⟨C$_6$H$_3$(Cl)⟩—NHCO—⟨cyclopropyl⟩—CH$_3$ | M.P. 95–96° C. |

Among the carboxamides (I), preferred are those wherein R is difluoromethyl, trifluoromethyl or 2,2,2-trifluoroethyl and X is fluorine, chlorine, bromine, methyl or trifluoromethyl. Particularly preferred are N-(3-chloro-4-difluoromethoxyphenyl)-1-methylcyclopropanecarboxamide (I: R=difluoromethyl; X=chlorine), N-(3-bromo-4-difluoromethoxyphenyl)-1-methylcyclopropanecarboxamide (I: R=difluoromethyl; X=bromine), N-(3-chloro-4-trifluoromethoxyphenyl)-1-methylcyclopropanecarboxamide (I: R=trifluoromethyl X=chlorine), etc.

Among the starting materials used for the production of the carboxamides (I), the compounds of the following formulas are novel:

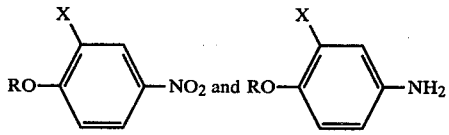

wherein R is difluoromethyl or trifluoroethyl and X is fluorine, chlorine, bromine or methyl, provided that when R is difluoromethyl, X is fluorine, bromine or methyl and when R is trifluoroethyl, X is chlorine.

On the practical usage of the carboxamides (I), they may be applied as such or in any conventional formulation such as wettable powders, emulsifiable concentrates, granules, fine granules, dusts or suspensions.

For production of said formulations, solid or liquid carriers or diluents may be used. As for the solid carrier or diluent, there may be exemplified mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be exemplified alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. If necessary, gelatin, casein, sodium alginate, starch, agar, polyvinyl alcohol or the like may be used as an auxiliary agent.

In the herbicidal composition of this invention, the content of the carboxamides (I) may be usually from 1 to 95% by weight, preferably from 5 to 80% by weight.

Practical embodiments of the herbicidal composition according to the invention are illustratively shown in the following examples wherein part(s) and % are by weight.

FORMULATION EXAMPLE 1

Eighty parts of Compound No. 1, 5 or 6, 5 parts of polyoxyethylene alkylaryl ether and 15 parts of synthetic silica hydrate are well mixed while being powdered to obtain a wettable powder.

FORMULATION EXAMPLE 2

Ten parts of Compound No. 1, 3 or 7, 7 parts of polyoxyethylene alkylaryl ether, 3 parts of alkylaryl sulfonate and 80 parts of xylene are well mixed to obtain an emulsifiable concentrate.

FORMULATION EXAMPLE 3

One part of Compound No. 1, 4 or 6, 1 part of white carbon, 5 parts of ligninsulfonate and 93 parts of clay are well mixed while being powdered. The mixture is then well kneaded with water, granulated and dried to obtain a granule.

FORMULATION EXAMPLE 4

Forty parts of bentonite, 5 parts of ligninsulfonate and 55 parts of clay are well mixed while being powdered. The mixture is then well kneaded with water, granulated and dried to obtain granules containing no active ingredient. The granules are then impregnated with 5 parts of Compound No. 1, 5 or 7 in acetone to obtain a granule.

FORMULATION EXAMPLE 5

Three parts of Compound No. 1, 2 or 6, 0.5 part of isopropyl phosphate, 66.5 parts of clay and 30 parts of talc are well mixed while being powdered to obtain a dust.

FORMULATION EXAMPLE 6

Twenty parts of Compound No. 1, 3 or 6 are mixed with 60 parts of an aqueous solution containing 3% polyoxyethylene sorbitan monolactate and ground until the particle size of the active ingredient becomes less than 3 microns. Twenty parts of an aqueous solution containing 3% of sodium alginate as a dispersing agent is introduced therein to obtain a suspension.

When desired, the carboxamides (I) may be used together with other herbicides to improve their herbicidal activity, and in some cases, to produce a synergistic effect. As the other herbicides, there may be exemplified 2,4-dichlorophenoxyacetic acid, sodium 5-[2-chloro-4-(trifluoromethyl)phenoxy]-2-nitrobenzoate, 2-chloro-4-ethylamino-6-isopropylamino S-triazine, 2-methylthio-4,6bis-(isopropylamino)-S-triazine, 3-(3,4-dichlorophenyl)-1,1-dimethylurea, 3-[4-(4-chlorophenoxy)phenyl]-1,1-dimethylurea, 3-($\alpha,\alpha,\alpha$-trifluoro-m-tolyl)-1,1-dimethylurea, isopropyl-N-(3-chlorophenyl)carbamate, 3,4-dichloropropyonanilide, 3-cyclohexyl-5,6-trimethyluracil, O-methyl-O-(2-nitro-5-methylphenyl)-N-sec-butylphosphoroamidothioate, 3-isopropyl-1H-2,1,3-benzothiadiazine(4)-3H-one-2,2-dioxide, disodium methanearsonate, and the like. However, the herbicides are not of course limited to these examples.

Also, the carboxamides (I) may be applied together with fungicides, microbicidal agricultural chemicals, organic phosphorus series insecticides, carbamate series insecticides, pyrethroid series insecticides, other insecticides, plant growth regulators, fertilizers, etc.

The dosage of the carboxamides (I) depends upon their kinds, the sorts of cultivated plants, the method of application, weather, etc. Generally, however, the dosage is from 0.5 to 50 grams, preferably from 2 to 20 grams, of the active ingredient per are.

The application of the carboxamides (I) as herbicides will be illustratively shown in the following Examples wherein the phytotoxicity to cultivated plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and to control weeds, respectively. The rating values in the paddy rice test alone were calculated from the dry weight of the plant.

| Rating value | Fresh Weight (percentage to untreated plot) | |
|---|---|---|
| | Cultivated plant | Weed |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the Examples:

| | Remarks |
|---|---|
| Control (a) [structure: dimethyl-CHO substituted chlorophenyl-NHCO-cyclopropyl-CH3] | Compound disclosed in U.S. Pat. No. 4,166,735 |
| Control (b) [structure: 2,4-dichlorophenyl-NHCO-cyclopropyl-CH3] | Compound disclosed in U.S. Pat. No. 3,277,171 |
| Diuron [structure: 3,4-dichlorophenyl-NHCON(CH3)2] | Commercially available herbicide |
| Fluometuron [structure: 3-CF3-phenyl-NHCON(CH3)2] | Commercially available herbicide |
| Bromoxynil [structure: 3,5-dibromo-4-hydroxybenzonitrile] | Commercially available herbicide |
| MCP [structure: 4-chloro-2-methylphenoxyacetic acid] | Commercially available herbicide |

TEST EXAMPLE 1

Plastic trays (35 cm × 25 cm × 10 cm) were filled with upland field soil, and the seeds of prickly sida, tall morningglory, cocklebur, jimsonweed, socklepod and barnyardgrass and the seeds of cotton were sowed in the trays and grown for 19 days in a greenhouse. The designed amount of the test compound formulated in an emulsifiable concentrate was sprayed to the foliage of the test plants over the top by means of a small hand sprayer. After the spraying, the test plants were grown for an additional 3 weeks in the greenhouse, and the herbicidal activity and phytotoxicity were examined. The results are shown in Table 1. In this treatment, the emulsifiable concentrate was dispersed in water for application at a spray volume of 5 liters per are.

The growing stage of the test plants varied depending on their kind. However, the weeds were generally at the 2 to 4 leaf stage and the cotton was at the first leaf stage.

designed amount of the test compound formulated in an emulsifiable concentrate was sprayed to the foliage of the test plants over the top by means of a small hand sprayer. After the spraying, the test plants were grown for an additional 3 weeks in the greenhouse, and the herbicidal activity and phytotoxicity were examined.

TABLE 1

| Compound No. | Dosage of active ingredient (g/are) | Phytotoxicity Cotton | Prickly sida | Tall morning-glory | Cocklebur | Jimsonweed | Sicklepod | Barnyard-grass |
|---|---|---|---|---|---|---|---|---|
| 1 | 10 | 0 | 5 | 5 | 5 | 5 | 5 | 5 |
|  | 5 | 0 | 5 | 5 | 5 | 5 | 5 | 5 |
|  | 2.5 | 0 | 5 | 5 | 5 | 5 | 4 | 4 |
|  | 1.25 | 0 | 4 | 3 | 5 | 5 | 3 | 2 |
| 2 | 10 | 1 | 5 | 5 | 5 | 5 | 5 | 5 |
|  | 5 | 0 | 5 | 5 | 5 | 5 | 5 | 4 |
|  | 2.5 | 0 | 5 | 4 | 4 | 5 | 3 | 2 |
|  | 1.25 | 0 | 3 | 3 | 2 | 4 | 2 | 1 |
| 3 | 10 | 1 | 5 | 5 | 5 | 5 | 5 | 5 |
|  | 5 | 0 | 5 | 5 | 5 | 5 | 5 | 5 |
|  | 2.5 | 0 | 5 | 5 | 5 | 5 | 5 | 4 |
|  | 1.25 | 0 | 5 | 4 | 5 | 5 | 4 | 3 |
| 4 | 10 | 0 | 5 | 5 | 5 | 5 | 5 | 5 |
|  | 5 | 0 | 5 | 5 | 5 | 4 | 4 | 4 |
|  | 2.5 | 0 | 3 | 4 | 3 | 5 | 3 | 2 |
| 5 | 10 | 1 | 5 | 5 | 5 | 5 | 5 | 5 |
|  | 5 | 0 | 5 | 5 | 5 | 5 | 5 | 4 |
|  | 2.5 | 0 | 4 | 5 | 5 | 5 | 4 | 4 |
|  | 1.25 | 0 | 4 | 3 | 4 | 5 | 2 | 2 |
| 6 | 10 | 1 | 5 | 5 | 5 | 5 | 5 | 5 |
|  | 5 | 0 | 5 | 5 | 5 | 5 | 5 | 5 |
|  | 2.5 | 0 | 5 | 5 | 5 | 5 | 4 | 3 |
|  | 1.25 | 0 | 4 | 4 | 5 | 5 | 2 | 2 |
| 7 | 10 | 0 | 5 | 5 | 5 | 5 | 5 | 5 |
|  | 5 | 0 | 5 | 5 | 5 | 5 | 5 | 4 |
|  | 2.5 | 0 | 5 | 4 | 5 | 5 | 4 | 4 |
|  | 1.25 | 0 | 3 | 4 | 4 | 5 | 3 | 2 |
| Control (a) | 10 | 3 | 5 | 5 | 5 | 5 | 5 | 5 |
|  | 5 | 2 | 4 | 4 | 5 | 5 | 3 | 4 |
|  | 2.5 | 2 | 2 | 3 | 4 | 3 | 1 | 2 |
|  | 1.25 | 1 | 2 | 1 | 2 | 2 | 1 | 0 |
| Control (b) | 10 | 2 | 5 | 5 | 5 | 5 | 4 | 5 |
|  | 5 | 1 | 4 | 4 | 5 | 5 | 4 | 4 |
|  | 2.5 | 1 | 3 | 4 | 4 | 5 | 1 | 2 |
|  | 1.25 | 0 | 1 | 3 | 3 | 3 | 0 | 1 |
| Diuron | 10 | 2 | 5 | 5 | 5 | 5 | 5 | 4 |
|  | 5 | 2 | 3 | 4 | 5 | 5 | 5 | 3 |
|  | 2.5 | 1 | 1 | 4 | 5 | 5 | 3 | 1 |
|  | 1.25 | 0 | 0 | 2 | 4 | 5 | 2 | 0 |
| Fluometuron | 20 | 1 | 3 | 5 | 5 | 5 | 5 | 3 |
|  | 10 | 0 | 2 | 4 | 5 | 5 | 4 | 2 |
|  | 5 | 0 | 0 | 3 | 3 | 4 | 2 | 2 |
|  | 2.5 | 0 | 0 | 1 | 1 | 2 | 1 | 0 |

TEST EXAMPLE 2

Plastic trays (35 cm×25 cm×10 cm) were filled with upland field soil, and the seeds of common lambsquarters, black nightshade, wild buckwheat, common chickweed and pansy and the seeds of wheat were sowed in the trays and grown for 3 weeks in a greenhouse. The The results are shown in Table 2. In this treatment, the emulsifiable concentrate was dispersed in water for application at a spray volume of 5 liters per are.

The growing stage of the test plants varied depending on their kind. However, the weeds were generally at the 2 to 4 leaf stage and the wheat was at the trifoliate stage.

TABLE 2

| Compound No. | Dosage of active ingredient (g/are) | Phytotoxicity Wheat | Common lambsquarters | Black nightshade | Wild buckwheat | Common chickweed | Pansy |
|---|---|---|---|---|---|---|---|
| 1 | 10 | 1 | 5 | 5 | 5 | 5 | 5 |
|  | 5 | 1 | 5 | 5 | 5 | 5 | 5 |
|  | 2.5 | 0 | 5 | 5 | 5 | 5 | 5 |
| 3 | 10 | 1 | 5 | 5 | 5 | 5 | 5 |
|  | 5 | 1 | 5 | 5 | 5 | 5 | 5 |
|  | 2.5 | 0 | 5 | 5 | 5 | 5 | 5 |
| 7 | 10 | 1 | 5 | 5 | 5 | 5 | 5 |
|  | 5 | 1 | 5 | 5 | 5 | 5 | 5 |
|  | 2.5 | 0 | 5 | 5 | 5 | 5 | 5 |
| Control (a) | 10 | 1 | 5 | 5 | 5 | 5 | 5 |

TABLE 2-continued

| Compound No. | Dosage of active ingredient (g/are) | Phytotoxicity Wheat | Herbicidal activity Common lambsquarters | Black nightshade | Wild buckwheat | Common chickweed | Pansy |
| --- | --- | --- | --- | --- | --- | --- | --- |
|  | 5 | 1 | 5 | 5 | 5 | 4 | 4 |
|  | 2.5 | 0 | 5 | 4 | 5 | 4 | 2 |
| Control (b) | 10 | 2 | 5 | 5 | 5 | 5 | 5 |
|  | 5 | 1 | 5 | 5 | 5 | 5 | 5 |
|  | 2.5 | 0 | 4 | 3 | 5 | 5 | 3 |
| Bromoxynyl | 10 | 1 | 5 | 5 | 5 | 1 | 4 |
|  | 5 | 1 | 5 | 5 | 5 | 0 | 2 |
|  | 2.5 | 0 | 5 | 5 | 3 | 0 | 1 |

TEXT EXAMPLE 3

Wagner's pots (1/5000 are) were each filled with paddy field soil, and the seeds of barnyardgrass, pickerel weed, false pimpernel and toothcup were sowed and thoroughly mixed at the depth of 2 cm from the soil surface. Water was poured therein until the depth of water became 4 cm. Rice seedlings at the trifoliate stage were transplanted into the pots and grown for 10 days in a greenhouse. The designed amount of the test compound formulated in an emulsifiable concentrate was applied to the pots by perfusion. Thereafter, the test plants were grown for an additional 20 days in the greenhouse, and the herbicidal activity and phytotoxicity were examined. The results are shown in Table 3. In this treatment, the emulsifiable concentrate was dispersed in water for application at a perfusion volume of 10 liters per are.

TABLE 3

| Compound No. | Dosage of active ingredient (g/are) | Phytotoxicity Rice plant | Herbicidal activity Barnyardgrass | Pickerel weed | False pimpernel | Toothcup |
| --- | --- | --- | --- | --- | --- | --- |
| 1 | 10 | 0 | 5 | 5 | 5 | 5 |
|  | 5 | 0 | 5 | 5 | 5 | 5 |
|  | 2.5 | 0 | 4 | 5 | 5 | 5 |
| 3 | 10 | 1 | 5 | 5 | 5 | 5 |
|  | 5 | 0 | 5 | 5 | 5 | 5 |
|  | 2.5 | 0 | 4 | 5 | 5 | 5 |
| 5 | 10 | 1 | 5 | 5 | 5 | 5 |
|  | 5 | 0 | 4 | 5 | 5 | 5 |
|  | 2.5 | 0 | 3 | 5 | 5 | 5 |
| 6 | 10 | 1 | 5 | 5 | 5 | 5 |
|  | 5 | 0 | 5 | 5 | 5 | 5 |
|  | 2.5 | 0 | 4 | 5 | 5 | 5 |
| Control (a) | 10 | 1 | 4 | 5 | 5 | 5 |
|  | 5 | 1 | 3 | 4 | 5 | 5 |
|  | 2.5 | 0 | 1 | 4 | 4 | 3 |
| Control (b) | 10 | 2 | 5 | 5 | 5 | 5 |
|  | 5 | 2 | 3 | 5 | 5 | 5 |
|  | 2.5 | 1 | 2 | 3 | 5 | 5 |
| MCP | 10 | 2 | 3 | 5 | 5 | 5 |
|  | 5 | 1 | 2 | 5 | 5 | 5 |
|  | 2.5 | 0 | 1 | 5 | 5 | 5 |

TEST EXAMPLE 4

The field as previously prepared and fertilized was divided into plots, each plot having an area of 2 m², and the seeds of cocklebur, tall morningglory, sicklepod, prickly sida and barnyardgrass and the seeds of cotton were sowed therein. Cultivation was carried out for 3 weeks. At the time when the cotton grew up to the first foliate stage and the weeds up to the 2 to 4 leaf stages, the designed amount of the test compound formulated in an emulsifiable concentrate and dispersed in water was sprayed to the test plants over the top by means of a small hand sprayer at a rate of 5 liters per are. After further cultivation for 3 weeks, the herbicidal activity and phytotoxicity were examined. The results are shown in Table 4.

TABLE 4

| Compound No. | Dosage of active ingredient (g/are) | Phytotoxicity Cotton | Herbicidal activity Cocklebur | Tall morningglory | Sicklepod | Prickly sida | Barnyard grass |
| --- | --- | --- | --- | --- | --- | --- | --- |
| 1 | 10 | 0 | 5 | 5 | 5 | 5 | 5 |
|  | 5 | 0 | 5 | 5 | 5 | 5 | 4 |
|  | 2.5 | 0 | 5 | 5 | 4 | 4 | 2 |
| 3 | 10 | 1 | 5 | 5 | 5 | 5 | 5 |
|  | 5 | 0 | 5 | 5 | 5 | 5 | 3 |
|  | 2.5 | 0 | 5 | 5 | 4 | 5 | 2 |
| 6 | 10 | 1 | 5 | 5 | 5 | 5 | 5 |
|  | 5 | 0 | 5 | 5 | 5 | 5 | 4 |
|  | 2.5 | 0 | 5 | 5 | 3 | 4 | 2 |
| Control (a) | 10 | 2 | 4 | 4 | 4 | 5 | 4 |
|  | 5 | 2 | 3 | 3 | 2 | 3 | 2 |

TABLE 4-continued

| Compound No. | Dosage of active ingredient (g/are) | Phytotoxicity Cotton | Herbicidal activity | | | | |
|---|---|---|---|---|---|---|---|
| | | | Cocklebur | Tall morning-glory | Sicklepod | Prickly sida | Barnyard grass |
| | 2.5 | 1 | 2 | 1 | 0 | 3 | 0 |
| Control (b) | 10 | 1 | 5 | 5 | 4 | 5 | 4 |
| | 5 | 1 | 4 | 4 | 3 | 3 | 2 |
| | 2.5 | 0 | 2 | 3 | 1 | 3 | 1 |
| Diuron | 10 | 2 | 5 | 5 | 5 | 4 | 3 |
| | 5 | 2 | 5 | 3 | 4 | 2 | 1 |
| | 2.5 | 0 | 4 | 2 | 3 | 0 | 0 |
| Fluometuron | 20 | 1 | 5 | 3 | 3 | 2 | 2 |
| | 10 | 0 | 3 | 3 | 2 | 1 | 2 |
| | 5 | 0 | 2 | 2 | 0 | 0 | 0 |

What is claimed is:

1. A compound of the formula:

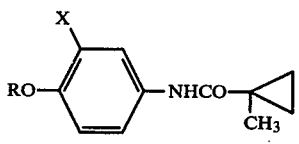

wherein R is a methyl or ethyl group substituted with two or three fluorine atoms and X is a halogen atom or a trifluoromethyl group.

2. The compound according to claim 1, wherein R is difluoromethyl, trifluoromethyl or 2,2,2-trifluoroethyl and X is fluorine, chlorine, bromine or trifluoromethyl.

3. The compound according to claim 1, wherein R is difluoromethyl and X is chlorine.

4. The compound according to claim 1, wherein R is difluoromethyl and X is bromine.

5. The compound according to claim 1, wherein R is trifluoromethyl and X is chlorine.

6. A herbicidal composition which comprises a herbicidally effective amount of the compound according to claim 1 and an inert carrier or diluent.

7. A method for exterminating weeds which comprises applying a herbicically effective amount of the compound according to claim 1 to the area where weeds are growing or will grow.

8. The method according to claim 7, wherein the area is a field of cotton.

* * * * *